United States Patent [19]

Courty et al.

[11] 4,207,169
[45] Jun. 10, 1980

[54] PROCESS FOR THE STEAM DEALKYLATION OF AROMATIC HYDROCARBONS

[75] Inventors: Philippe Courty, Houilles; Germain Martino, Poissy; Jean-François Le Page, Rueil Malmaison, all of France

[73] Assignee: Institut Francais du Petrole, Rueil-Malmaison, France

[21] Appl. No.: 1,653

[22] Filed: Jan. 8, 1979

[30] Foreign Application Priority Data

Jan. 6, 1978 [FR] France ................... 78 00335

[51] Int. Cl.² .................. C07C 3/58; B01J 23/64; C10G 11/02; C10G 35/08
[52] U.S. Cl. .................. 208/124; 208/112; 208/138; 252/466 PT; 585/487
[58] Field of Search .............. 208/112, 124, 138; 252/466 PT; 260/672 R; 585/487

[56] References Cited

U.S. PATENT DOCUMENTS

| 3,197,523 | 7/1965 | Michalko et al. ............. 585/488 |
| 3,436,433 | 4/1969 | Lester ................... 585/487 |
| 3,595,932 | 7/1971 | Maslyansky et al. ........... 585/487 |
| 3,649,706 | 4/1972 | Lester ................... 585/487 |
| 3,649,707 | 4/1972 | Lester ................... 585/487 |
| 4,013,734 | 3/1977 | Kim ..................... 585/487 |

FOREIGN PATENT DOCUMENTS

| 2139043 | 2/1972 | Fed. Rep. of Germany ........ 208/124 |
| 2317962 | 2/1977 | France ................. 585/487 |
| 76/39588 | 4/1976 | Japan .................. 208/124 |
| 213776 | 3/1971 | U.S.S.R. ............... 208/124 |

*Primary Examiner*—Delbert E. Gantz
*Assistant Examiner*—G. E. Schmitkons
*Attorney, Agent, or Firm*—Millen & White

[57] ABSTRACT

Catalytic process for steam dealkylation of a charge containing at least one alkyl aromatic hydrocarbon, such as a charge issued from effluents of units for catalytic reforming or for producing aromatic hydrocarbons, wherein the catalyst contains an alumina carrier, from 0.1 to 1% of rhodium, from 0.05 to 1% of $TiO_2$ and optionally from 0.1 to 1% of ruthenium, palladium, iridium, platinum or osmium and/or from 0.01 to 5% of lithium, sodium, potassium, rubidium or cesium.

14 Claims, 1 Drawing Figure

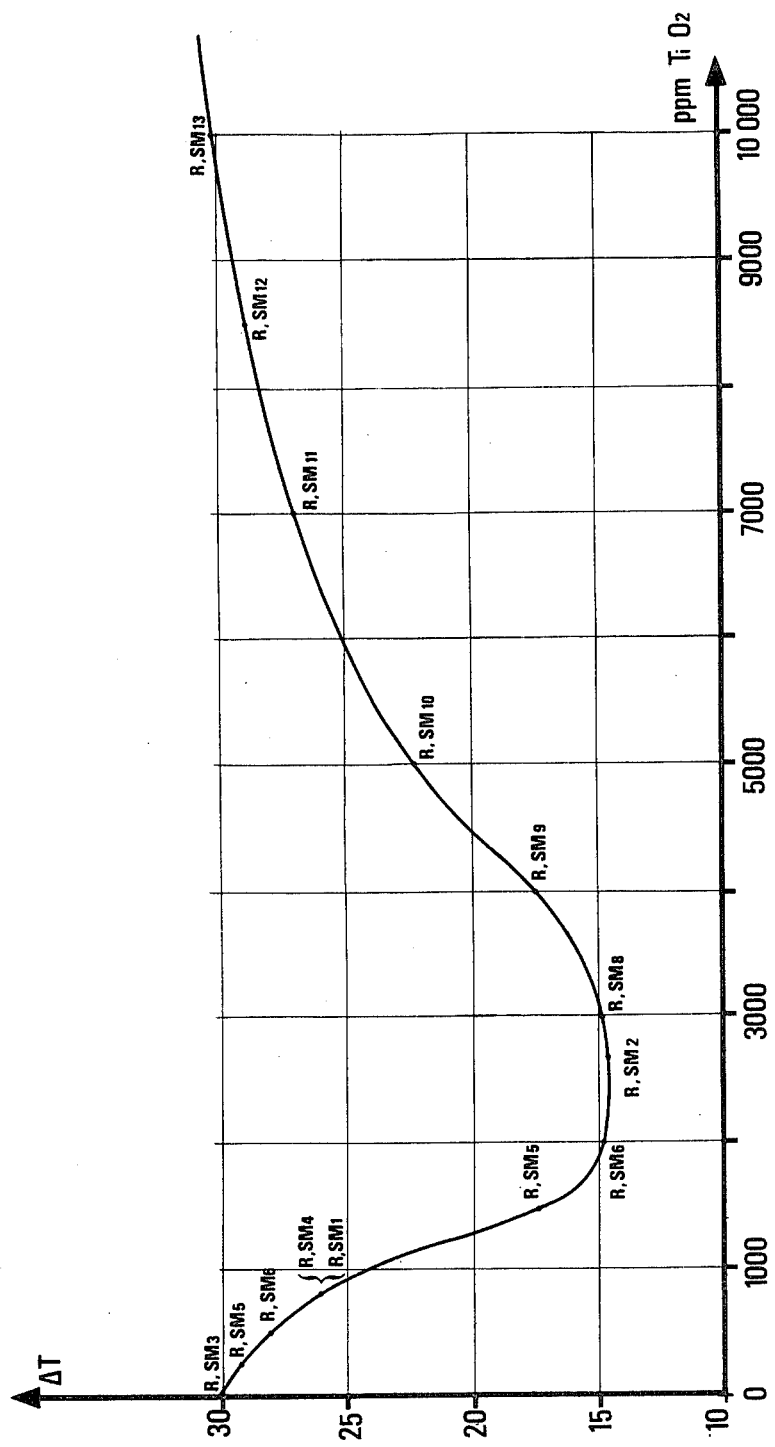

PROCESS FOR THE STEAM DEALKYLATION OF AROMATIC HYDROCARBONS

BACKGROUND OF THE INVENTION

This invention relates to steam dealkylation reactions for producing benzene or its lower homologs by dealkylation of toluene and of other alkylbenzenes.

A number of catalysts have been proposed for the steam dealkylation of aromatic hydrocarbons, these catalysts containing a porous carrier and at least one metal deposited on the carrier. By way of examples, there can be mentioned:

USSR Patent specification No. 213 776, disclosing a catalyst containing rhodium, nickel and alumina;

U.S. Pat. No. 3,595,932, disclosing a catalyst containing a noble metal of the platinum family (platinum, palladium, rhodium, iridium, ruthenium) on a carrier consisting of alumina or combinations of alumina with nickel or cobalt;

U.S. Pat. No. 3,436,433, disclosing a catalyst containing alumina, an alkali metal, ferric oxide, rhodium and chromium;

U.S. Pat. Nos. 3,649,706 and 3,649,707, disclosing catalysts containing mixtures of an alkali metal with ferric oxide, chromium and a metal selected from platinum, palladium and rhodium;

U.S. Pat. No. 4,013,734, disclosing a catalyst containing alumina, a noble metal of the platinum family and a metal selected from vanadium, niobium and tantalum;

French Pat. No. 2,317,962 to Cerciat and Szabo (equivalent to Ger. Pat. No. 2,629,647), disclosing a catalyst containing alumina and alumina-silicas in addition to rhodium and a metal from group IV A, particularly tin.

The catalysts used up to now suffer from a clearly insufficient stability, this lack of stability resulting in rapid deactivation and rapid mechanical disaggregation of the catalyst.

BRIEF DESCRIPTION OF THE DRAWING

The drawing is a plot of the temperature increase required to maintain a conversion rate of 65% for 1,000 hours, in relation to the $TiO_2$ content of the catalyst carrier.

OBJECTS OF THE INVENTION

The present invention has for object to obviate these major disadvantages by providing a process whereby the yield of final product may be increased by the selection of stable catalysts.

DETAILED DISCUSSION

This object is achieved by preparing benzene and/or its lower homologs by dealkylation of alkyl benzenes (toluene, xylenes, etc.) by steam conversion in the presence of specific catalysts.

The operating temperature is usually from 300° to 600° C., preferably from 350° to 550° C. and the pressure is usually from 1 to 20 atmospheres and preferably from 3 to 10 atmospheres, while the LHSV ("Liquid hourly Space velocity) i.e. a liquid VVH (space velocity) is from 0.1 to 10 volumes of hydrocarbons per volume of catalyst and per hour (preferably from 1 to 5), with a ratio (by moles) $H_2O$/hydrocarbons from 1 to 20, preferably from 3 to 15.

During the process there is obtained total dealkylation products like benzene as well as partial dealkylation products like, for example, toluene from xylenes.

More precisely, the process provides for the production of benzene, toluene, xylenes, ethylbenzene with substantial hydrogen amounts. According to this process, it is possible, for example, to dealkylate toluene, xylenes, ethylbenzene, propylbenzene, methylbenzene or even hydrocarbons with condensed rings such as naphthalene, phenanthrene, anthracene, etc. There can also be mentioned mesitylene, pseudocumene, hemimellitene; the process can also be used for aromatization followed with dealkylation of such hydrocarbons as alkylcyclohexane, alkyltetrahydronaphthalene, alkyldecahydronaphthalene and alkyldihydroanthracene.

According to this process, nitrogenous aromatic compounds, such for example as pyridine derivatives, may also be dealkylated, nitrogen being eliminated as $NH_3$ or $N_2$.

The process is of particular efficiency for dealkylating alkyl aromatic hydrocarbons recovered from catalytic reforming reactions or reactions for producing aromatic hydrocarbons (call "Aromizing reactions").

The specific catalysts used according to this invention contain:

(a) - a carrier (b) - from 0.1 to 1%, preferably 0.2 to 0.8% and more particularly 0.25 to 0.65% by weight, with respect to the catalyst, of rhodium.

(c) - 0.05 to 1%, preferably 0.06 to 0.05% and more particularly 0.07 to 0.3% of titanium oxide of formula $TiO_2$, expressed by weight with respect to the catalyst.

Preferably, the specific catalysts of the invention contain:

(a) - A carrier containing, by weight, 0.05 to 1%, preferably 0.06 to 0.5% and more particularly 0.07 to 0.3% of titanium oxide of formula $TiO_2$;

(b) - 0.1 to 1%, preferably 0.2 to 0.8% and more particularly 0.25 to 0.65%, expressed by weight with respect to the catalyst, of rhodium.

There can be further used 3 preferred types of catalysts according to the invention: (catalysts No. 1 to 3) as defined hereinafter:

Catalyst No. 1

These catalysts contain, in addition to titanium and rhodium, and expressed by weight with respect to the catalyst, 0.1 to 1%, preferably 0.2 to 0.8% and more particularly 0.25 to 0.65%, of at least one noble metal of the platinum family, selected from ruthenium, palladium, iridium, platinum and osmium, ruthenium, palladium and platinum being the preferred metals.

Catalyst No. 2

These catalysts, in addition to titanium and rhodium, contain 0.01 to 5% by weight, with respect to the catalyst, of at least one alkali metal selected from lithium, sodium, potassium, rubidium and cesium; rubidium and more particularly potassium and sodium being the preferred metals.

Catalyst No. 3

These catalysts contain, in addition to titanium and rhodium, at least one other noble metal, like catalyst No. 1 and an alkali metal, like catalyst No. 2.

Finally, to each of catalysts No. 1, No. 2 and No. 3, there can be added from 0.01 to 6%, by weight with respect to the catalyst, of at least one additional metal or compound of an additional metal selected from indium, zirconium, thorium, germanium, tin, vanadium, niobium, tantalum, chromium, molybdenum, tungsten, manganese, rhenium, iron, cobalt and nickel. The preferred metals are indium, tungsten, tantalum, tin, manganese, chromium, molybdenum and iron and more particularly niobium, cobalt, vanadium, nickel, germanium and rhenium.

The aluminas used as carrier in the preparation of the catalysts of the invention may be produced by processes making use of an alkaline attack of minerals of the bauxite type, as according to the BAYER process. They may also be obtained by processes making use of an acid attack of clay or shale minerals such as in the H+PECHINEY process. They can be preferably produced by processes comprising the step of dissolving aluminum into an alcohol, followed with the hydrolysis of the alcoholate, such methods being described in U.S. Pat. Nos. 2,636,865, 2,762,782, 2,762,783, 2,905,632 and 3,006,864.

They can also be obtained, preferably in accordance with the teaching of U.S. Pat. No. 2,892,858 to ZIEGLER, by hydrolysis of aluminum alkoxides obtained by addition of ethylenic hydrocarbons onto a trialkylaluminum and by oxidation of a polyalkylaluminum to a polyalkoxyaluminum.

The catalysts of the invention are preferably prepared by adding, in a first step, 0.05 to 1% of titanium dioxide onto the alumina carrier. Any process for effecting said addition of titanium dioxide is convenient. For example, the titanium compound can be dissolved in a solution containing the aluminum compound and the precipitation conditions of the alumina may be so adjusted that the titanium hydroxide coprecipitates. It is also possible to add to the hydrated alumina in the form of a gel ($\alpha$-trihydrate, $\beta$-trihydrate or $\alpha$-monohydrate of aluminum) at least one titanium compound selected from the group consisting of titanium dioxide as rutile and anatase, the suboxides TiO and $Ti_2O_3$, the titanium acids, the alkaline, earth-alkaline and ammonium titanates and the soluble and insoluble, organic and inorganic titanium salts.

It is also possible to start with a shaped alumina carrier and impregnate it with a solution of an organic or inorganic titanium salt; as a general rule, the addition of titanium may be conducted before, during or after the step of shaping the catalyst carrier.

A preferred process consists of adding at least one titanium organic compound, for example tetraethoxytitanium to an organic (for example alcoholic) solution of at least one aluminum organic compound (for example an alkoxyaluminum compound such as aluminum isopropylate), and then of hydrolysing the resulting solution.

It is also possible to add titanium in the form of an easily hydrolysable inorganic compound such as titanium tetrachloride $TiCl_4$.

Another preferred process consists of adding controlled amounts of a titanium organic compound, for example an alkoxytitanium compound such as tetraethyltitanium and/or an inorganic titanium compound (for example titanium trichloride) in the course of the ZIEGLER synthesis of the polyalkoxyaluminum compound, by reacting an alkyl aluminum compound (for example triethylaluminum) with ethylene and at least one of the above-mentioned titanium compounds. By polymerization and subsequent oxidation, the above-mentioned polyalkoxy aluminum compound is prepared, whose hydrolysis will lead to polyols and titanium-containing hydrated alumina.

It has been observed, by experiment, that these processes resulted in a particularly high dispersion of the titanium ions in the alumina matrix, obtained after hydrolysis of the alkoxy aluminum or polyalkoxy aluminum compound. The preferred processes for impregnating titanium are such as to obtain, for example when the carrier is in the form of balls or extrudates etc. a steady $TiO_2$ content from one ball to another or from one extrudate to another; the average desired concentration being C %, the concentration C in any ball or extrudate will remain, according to the preferred methods of the invention, in the range of C±5% and even ±3% by weight. Still improved results have been obtained by using catalyst carriers containing more particularly from 0.06 to 0.5% of $TiO_2$.

In a second step, the catalyst carrier, which contains from 0.05 to 1% of $TiO_2$, is impregnated with one or more solutions containing one or more active elements, and then dried and thermally activated.

The catalyst carrier according to the invention is preferably selected from eta-cubic $\eta$, gamma-cubic $\gamma_C$, tetragonal gamma $\gamma_T$, Chi cubic $\chi$, kappa-orthocubic $\kappa$, theta-monoclinic $\theta$, delta-ortho rhombic $\delta$ and rho-amorphous $\rho$ aluminas.

It has a specific surface from 2 to 400 m$^2$/g and preferably from 50 to 350 m$^2$/g and a total pore volume from 30 to 150 ml/100 g.

It further comprises, by weight, from 0.05 to 1%, more particularly from 0.06 to 0.5%, and still more preferably from 0.07 to 0,3% of $TiO_2$, said titanium oxide being introduced preferably onto the carrier, before the introduction of the one or more metals or metal compounds contained in the final catalyst.

The carrier is then impregnated, for example, with an aqueous solution of rhodium or of rhodium in admixture with a metal from the platinum family (if any), then the carrier is dried and thermally activated (calcination and/or reduction) and then it is impregnated (optionally and for example with at least one of said additional metals), dried, then impregnated, if necessary, with an alkali metal. Final drying is performed, followed with thermal activation (calcination and/or reduction).

For example, the drying step is performed at 100° C. and then at 200° C. for 1 hour or more.

Calcination is performed at a temperature from 300° to 500° C. for 1 hour or more.

Reduction is conducted at 200° to 400° C. in the presence of a gas containing at least 10% $H_2$ for 1 hour or more.

During the dealkylation reactions, the catalysts are preferably maintained at a constant conversion rate in the range from 40 to 75% molar, by progressively raising the temperature of the test. The deactivation rate over, for example, 2000 hours of test, is defined in degrees C/1000 hours, and expressed by the ratio:

$$V = \frac{\text{Final } T - \text{Initial } T}{2000} \times 1000$$

By way of example, for a catalyst which has been used for 2000 hours 400° C. (Initial T) to 550° C. (Final T), the deactivation rate is:

$$V = \frac{550 - 400}{2000} \times 1000 = 75° \text{ C.}/1000\, h$$

The following examples illustrate the invention: In Tables I to X, the proportions of metal elements or compounds are expressed by weight. The benzene yields and the conversion rates are expressed in mole %.

EXAMPLE 1

Preparation of carriers $SA_1$ to $SA_7$

An alumina carrier, available commercially, consisting of extrudates of $\gamma_C$ and $\gamma_T$ aluminas, having a specific surface of 230 m$^2$/g, a pore volume of 54 ml/100 g, a diameter of 1.2 mm and lengths from 5 to 7 mm, is divided in 7 fractions of 100 g ($SA_1$ to $SA_7$):

Portion $SA_1$ is roasted for 1 hour at 500° C.;

Portion $SA_2$ is impregnated with 0.4 g of decahydrated titanium oxalate in aqueous solution (0.06 g TiO$_2$), then dried at 100° C. for 1 hour, at 200° C. for 1 hour, and roasted at 500° C. for 1 hour;

The preparations $SA_3$ to $SA_7$ are performed in a similar way, with various amounts of titanium oxalate, resulting in various final contents of TiO$_2$.

The characteristics of carriers $SA_1$ to $SA_7$ are indicated below:

|  | weight of titanium oxalate (g) | % TiO$_2$ (weight) |
| --- | --- | --- |
| SA$_3$ | 0.68 | 0.10 |
| SA$_4$ | 1.36 | 0.20 |
| SA$_5$ | 2.03 | 0.30 |
| SA$_6$ | 3.40 | 0.50 |
| SA$_7$ | 5.41 | 0.80 |
| SA$_2$ | 0.40 | 0.06 |
| SA$_1$ | 0.00 | 0.00 |

The TiO$_2$ contents are not very different from one extrudate to another, the difference being not more than 5% by weight of the average TiO$_2$ content.

EXAMPLE 2

Test series A

Carriers $SA_1$ to $SA_7$, as identified in example 1, are then impregnated with an active substance, as described below:

100 g of carrier are immersed in distilled water and then dried at 80° C., so as to reduce their water content to 5% by weight.

They are then contacted with 100 ml of a solution containing 0.6 g of rhodium in the form of rhodium trichloride and 4 ml of pure hydrochloric acid ($d_{20°C.}$ = 1.19); after exhaustion of the solution (rhodium cannot be detected by adding stannous chloride to the solution), the catalyst is filtered, dried for 2 hours at 100° C., 2 hours at 200° C., then reduced under hydrogen atmosphere for 1 hour at 300° C.

The reduced catalyst is impregnated with 1% by weight of K$_2$O in the form of aqueous potassium carbonate, then dried for 2 hours at 100° C. and 2 hours at 200° C. The activation is conducted for 2 hours at 400° C.

This operation is repeated seven times and there are obtained catalysts $A_1$ to $A_7$ which all contain 0.6% of rhodium and 1% of K$_2$O by weight and additional titanium amount, as above mentioned.

Catalysts $A_1$ to $A_7$ are tested for 1000 hours in the presence of pure toluene at a 99.9% weight purity, containing 0.2 ppm of S. The results are reported in Table I.

TABLE I

Series A test conditions (MOLAR CONVERSION = 46%)

Charge : toluene
Pressure : 7 atmospheres
L.H.S.V. TOLUENE = 1 volume/catalyst volume/hour
H$_2$O/TOLUENE = 7 mole/mole
TEST DURATION = 1000 hours

| CATA-LYST | Initial T | Final T | DEACTI-VATION per 1000 h (°C.) | INITIAL YIELD | FINAL BENZENE (%) |
| --- | --- | --- | --- | --- | --- |
| A$_1$ | 420 | 465 | 45 | 40 | 39 |
| A$_2$ | 420 | 460 | 40 | 40 | 39 |
| A$_3$ | 415 | 449 | 34 | 41 | 40.5 |
| A$_4$ | 419 | 450 | 31 | 40.5 | 41 |
| A$_5$ | 422 | 454 | 32 | 41 | 40 |
| A$_6$ | 425 | 460 | 35 | 41.5 | 39.7 |
| A$_7$ | 430 | 470 | 40 | 40 | 39 |

These results show that, unexpectedly, the addition of TiO$_2$ to the alumina carrier has the effect of reducing the deactivation rate of the catalyst.

EXAMPLE 3

Test series B

A series of comparative tests is now conducted with the couple rhodium-ruthenium, associated with potassium.

Carriers $SA_1$ to $SA_7$ whose preparation has been describe in example 1, are used:

the preparation of series A is reproduced except that the 0.6 g of rhodium is replaced with 0.3 g of rhodium and 0.4 g of ruthenium in the form of trichlorides and 5 ml of HCl are added instead of 4 ml, the drying and activation steps being similar;

the impregnation is conducted with 1.8% of K$_2$O in the form of potassium carbonate and it is followed with a drying step for 2 hours at 100° C. and 2 hours at 200° C. Activation is then performed for 2 hours at 400° C. in air.

There is observed, similarly, a stabilizing effect of TiO$_2$ on the activity (Table II, series B). The operation is conducted in the test conditions of series A.

EXAMPLE 4

Test series C

Series B is reproduced except that ruthenium is replaced with palladium and potassium with sodium. Accordingly, the preparation of the catalyst $A_5$ is reproduced by replacing the 0.6 g or rhodium with 0.3 g of rhodium and 0.4 g of palladium in the form of chlorides and by adding 3 ml of HCl instead of 4 ml; the drying and activation steps being unchanged.

A subsequent impregnation is then conducted with 1.8% by weight of Na$_2$O in the form of sodium carbonate, followed with drying for 2 hours at 100° C. and 2 hours at 200° C.; activation is conducted at 400° C. for 1 hour in air.

The operation has been performed in the test conditions of series A. The results are given in Table III, series C.

EXAMPLE 5

Test series D

The preparation of catalyst $A_5$ of series A is reproduced except that a portion of rhodium is replaced with iridium and potassium with rubidium. For this purpose, the preparation of catalyst A$_5$ is reproduced with the replacement of the 0.6 g of rhodium with 0.3 g of rhodium and 0.4 g of iridium in the form of chlorometallic acids and with the addition of 4 ml of HCl. The drying step (at 100° C. for 2 hours) is followed with roasting at 400° C. for 2 hours and reduction at 300° C. for 1 hour.

The reduced catalyst is then impregnated with 0.8% of Rb$_2$O in the form of carbonated rubidium hydroxide in alcohol solution, dried for 2 hours at 100° C. and 2 hours at 200° C. and activated for 1 hour at 500° C.

The effect of rubidium is more important than that of potassium and accordingly, the Rb$_2$O content has been reduced from 1.8 to 0.8%.

As precedingly, titanium has a stabilizing effect on the activity.

The operation has been conducted in the test conditions of series A (The results are reported in Table IV, series D).

EXAMPLE 6

Test series E.

With the use of carrier SA$_3$, the preparation of series A test is reproduced while replacing the 0.6 g of rhodium with 0.3 g of rhodium and 0.4 g of platinum in the form of chlorides and by adding 4 ml of HCl: the drying step is conducted at 100° C. for 2 hours and then at 200° C. for one hour and is subsequently followed with a roasting in air at 400° C. for 2 hours.

The catalyst is thereafter impregnated with 1% of K$_2$O in the form of aqueous K$_2$CO$_3$, followed with drying at 250° C. for 2 hours and reduction in H$_2$ atmosphere at 300° C. for one hour.

The obtained results are reported in Table V (series E).

EXAMPLE 7

Preparation of series SF carriers.

Preparation of carrier SF$_1$: Under stirring, 4100 g of pure aluminium triisopropoxide Al(C$_3$H$_7$O)$_3$ are hydrolyzed in solution in 4500 ml of isopropanol, by means of 5000 ml of water.

The resulting precipitate is dried for 5 hours at 100° C., then placed in a pill shaper and agglomerated to balls having a size from 1.8 to 3 mm. The balls are dried and roasted at 550° C. for 4 hours. The fraction corresponding to a grain size from 1.6 to 2.5 mm is separated by sieving. 800 g of balls are obtained at each run; their porosity is 55 ml/100 g of which 10 ml/100 g correspond to pores of a diameter larger than 100 Å. Their specific surface is 210 m$^2$.g$^{-1}$.

Preparation of carrier SF$_2$: The preparation of SF$_1$ is reproduced up to the hydrolysis step.

The resulting hydrated alumina cake is admixed with 1 g of TiO$_2$ in the form of a titanic acid gel, obtained by oxidizing hydrolysis of a titanium trichloride solution. The admixing of the wet components is effected with a mixer (HOBBART) for 1 hour. After admixing, the resulting paste is dried at 100° C. for 8 hours, then crushed to semolina of grain size smaller than 0.5 mm and then agglomerated in a pill shaper to balls of a size from 1.8 to 3 mm; after drying, the balls are roasted at 550° C. for 3 hours. There is obtained 805 g of balls (1.6–2.5 mm) containing 0.12% of TiO$_2$ (average content). (A statistical analysis shows that this content varies from 0.08 to 0.15%). Their porosity is 50 ml/100 g of which 4 ml/100 g have a size greater than 100 Å. The surface is 230 m$^2$ per gram.

Preparation of carrier SF$_3$: 2.8 g of tetraethoxytitanium (about 0.97 g of TiO$_2$) are dissolved in an alcoholic solution of aluminum isopropylate; the hydrolysis is then performed as in the case of the preparation of the carrier SF$_1$. The preparation is otherwise identical to that of carrier SF$_1$.

There is obtained 803 g of balls (1.6–2.5 mm) containing 0.12% by weight of TiO$_2$; the statistical analysis shows that this content is substantially constant from one ball to another; the survey with a CASTAING microsonde of a ball section shows that TiO$_2$ is homogeneously distributed in each ball; the concentration varies from one ball to another, about 0.12%±0.2% of 0.12% (by weight).

The porosity of carrier SF$_3$ is 56 ml/100 g (of which 6 ml/100 g correspond to a pore diameter greater than 100 Å). The specific surface is 205 m$^2$.g$^{-1}$.

EXAMPLE 8

Test series F

This test has for object to prepare various catalysts with carriers SF$_1$, SF$_2$ and SF$_3$.

Preparation of a catalyst F$_1$: 100 g of alumina (carrier SF$_1$) are immersed in distilled water and then dried at 80° C. in order to reduce their water content to 6% by weight.

This alumina is then immersed in 100 ml of a solution containing 0.5 g of rhodium (in the form of chlorohodic acid), 0.3 g of indium (in the form of indium nitrate) and 3 ml of pure HCl (d=1.19). After exhaustion of the solution to an extent of more than 99%, the catalyst is fritted, dried for 2 hours at 100° C., then for 3 hours at 200° C., roasted in air at 400° C. for one hour and then reduced under hydrogen atmosphere at 300° C. for 2 hours.

1% of Na$_2$O is then added in the form of aqueous di-sodium carbonate, a drying step is then performed at 100° C., then at 200° C. and is followed with a roasting step for 2 hours at 430° C.

Preparations of catalysts F$_2$ and F$_3$: The preparation of catalyst F$_1$ is repeated, except that carriers SF$_2$ and SF$_3$ are respectively used.

The catalysts of series F are tested in the following conditions:
Charge:
pure toluene containing 99.8% by weight of toluene and 0.2 ppm of sulfur;
Pressure = 5 atmospheres
L.H.S.V. toluene = 2 volumes/catalyst volume/hour
H$_2$O/toluene = 5 mole$^1$/mole
Test duration = 1000 hours.

The results of the catalyst tests (Table VI, series F) confirm the influence of TiO$_2$. Carrier SF$_2$, which contains 0.12% of TiO$_2$, irregularly distributed, gives poorer results than the carrier SF$_3$ which contains 0.12% of well dispersed TiO$_2$.

EXAMPLE 9

Test series G.

Carriers SF$_1$ (0% TiO$_2$) and SF$_3$ (0.12% TiO$_2$) are compared in a catalyst formula containing rhodium, ruthenium and germanium and prepared as follows:

Preparation of catalyst G$_1$: 100 g of carrier SF$_1$ moistened with 0.3% by weight of H$_2$O are impregnated in a pill shaper with 55 ml of a solution containing 0.35 g of rhodium in the form of (RhCl$_3$), 0.35 g of ruthenium in the form of (RuCl$_3$), 5 g of citric acid mono-hydrate and 1% of germanium in the form of germanyl citrate. After 4 hours of maturation in air, the catalyst is dried at 100° C. for 5 hours and then roasted at 450° C. for 2 hours in air and finally reduced at 350° C. for 2 hours.

Preparation of catalyst $G_3$: The preparation is similar to that of catalyst $G_1$, but with the use of carrier $SF_3$. The comparative test (Table VII, series G) in the conditions of series F shows an undeniable stabilizing effect of titanium on the performances.

EXAMPLE 10

Test series H.

Similarly, the carriers $SF_1$ (0.0% $TiO_2$) and $SF_3$ (0.12% $TiO_2$), are compared in a catalyst formula containing rhodium, tin and potassium and prepared as follows:

Preparation of catalyst $H_1$: 100 g of carrier $SF_1$ (0% $TiO_2$), moistened at 0.8% by weight of $H_2O$, are impregnated in a dry state with 0.4% of tin in the form of a stannous chloride hydrochloric solution containing 4 moles of HCl per liter. The product dried for 2 hours at 200° C. and activated at 460° C. for 2 hours is contacted with 100 ml of a solution containing 0.7 g of rhodium in the form of ($RhCl_3$) and 5 ml of HCl. After fixation of 0.6 g of rhodium by anionic exchange, the carrier is washed twice with 200 ml of water, dried at 100° C. and then at 200° C. for 2 hours and reduced with hydrogen at 350° C. for 3 hours. It is finally impregnated with 0.2% of $K_2O$ in the form of an alcoholic solution of di-potassium carbonate and then activated at 400° C. for 2 hours in air.

Preparation of catalyst $H_3$: The preparation of catalyst $H_1$ is repeated except that the carrier is $SF_3$ (0.12% $TiO_2$). The comparative test (Table VII, series H), effected in the test conditions of series F, shows again the enhancing effect of the titanium-containing carrier ($SF_3$) on the stability of the catalysts.

EXAMPLE 11

Test series I

Carriers $SF_1$ (0% $TiO_2$) and $SF_3$ (0.12% $TiO_2$) are again compared in a catalyst formula containing rhodium, palladium and vanadium and prepared as follows:

Preparation of catalyst $I_1$: 100 g of $SF_1$ carrier are impregnated with 5 % by weight of vanadium pentoxide in the form of aqueous vanadyl oxalate. The catalyst is dried at 100° C. and then at 200° C. for 2 hours, and is thereafter reduced at 500° C. for 3 hours ($H_2$, 30% in $N_2$).

The reduced catalyst is impregnated with 48 ml of a solution containing 0.4 g of palladium, 0.3 g of rhodium in the form of chlorides and 4 ml of HCl. After maturation for 3 hours, the resulting product is dried at 150° C. for 6 hours and reduced with pure hydrogen at 350° C. for 1 hour.

Preparation of catalyst $I_3$: The preparation of catalyst $I_1$ is repeated, except that the carrier consists of 100 g of $SF_3$. The comparative test, in the operating conditions of the series F (Table VII, series I), shows that these catalysts are particularly active but that they are insufficiently stable in the presence of titanium.

EXAMPLE 12

Test series J

There is now used carrier $SF_3$ (0.12% of $TiO_2$) in a catalyst formula which differs from the formula of catalysts I in that palladium is replaced with platinum and the aqueous vanadyl oxalate solution, corresponding to 5% of $V_2O_5$, is replaced with an alcoholic solution containing 3% of $Ta_2O_5$ and 2% of $Nb_2O_5$ as chlorides. The remaining portion of the preparation is identical to that of catalysts I.

The results are summarized in Table VIII series J.

Table VIII, series K and L, show the results obtained with a catalyst containing (by weight):

(a) - 0.12% of $TiO_2$
(b) - 0.55% of rhodium
(c) - 1.5% of $K_2O$ and
(d) - chromium oxide (series K) and a mixture of $MoO_3 + WO_3$ (series L).

EXAMPLE 13

There is now prepared a series of carriers with reference $SM_1$ to $SM_{13}$.

Preparation of carrier $SM_1$: A polyalkoxyaluminum issued from a ZIEGLER synthesis unit (according to U.S. Pat. No. 2,892,858) in the presence of triethylaluminum, ethylene and a minimum amount of homogeneous catalyst on a titanium base (for example $TiCl_3$) is hydrolysed, washed and then dried by atomization at 200° C. There is obtained a fine powder formed of particles whose size is in the range from 20 to 150$\mu$ and having a surface of 230 m$^2$/g.

This powder is agglomerated in a pill shaper into balls of a size comprised between 1.8 and 3 mm. The balls are progressively dried and roasted at 550° C. for 4 hours. The grain fraction 1.6–2.5 mm is sieved.

The resulting carrier consists of a mixture of $\gamma_c$ and $\gamma_T$ aluminas and contains 0.08% of $TiO_2$, its surface being 205 m$^2$/g and its pore volume 55 ml/100 g.

Preparation of carrier $SM_2$: The same synthesis is conducted with a larger amount of titanium catalyst. There is obtained a carrier containing 0.27% of $TiO_2$, having a surface of 220 m$^2$/g and a pore volume of 52 ml/100 g.

Preparation of carrier $SM_3$: Under stirring, 8200 g of aluminum triisopropoxide $Al(C_3H_7O)_3$ for analysis are hydrolysed in 9000 ml of distilled water.

The resulting suspension is dried by atomization and then agglomerated in a pill shaper as for carrier $SM_1$; the drying and roasting steps being identical.

There is obtained 1600 g of balls having a porosity of 54 ml/100 g of which 11 ml/100 g have a size greater than 100 Å. The surface is 200 m$^2$/g; the carrier contains no $TiO_2$.

Preparation of carrier $SM_4$: The synthesis of carrier $SM_3$ is repeated while dissolving, in an alcoholic solution of aluminum isopropylate, 4.2 g of tetraethoxytitanium (about 1.45 g $TiO_2$). The other steps of the preparation are identical. There is obtained 1605 g of balls containing 0.08% of $TiO_2$, whose composition is identical to that of carrier $SM_1$.

Preparation of carriers $SM_5$ to $SM_{13}$: A series of carriers have been prepared (Table IX) in the same manner as above, by varying the amount of $TiO_2$ added to the alumina.

The $TiO_2$ contents of carriers $SM_1$ to $SM_{13}$ vary from 0.00 (carrier $SM_3$) to 1.01% (carrier $SM_{13}$) and are reported in Table IX below.

The carriers containing $TiO_2$ have a $TiO_2$ content which, from one ball to another, does not vary by more than 2% with respect to the average $TiO_2$ content of the carrier.

TABLE IX

ALUMINUM CARRIERS DOPED WITH TiO₂

| CARRIER No. | TiO$_2$ CONTENT (% by weight) | CARRIER No. | TiO$_2$ CONTENT (% by weight) |
|---|---|---|---|
| SM$_3$ | 0.00 | SM$_7$ | 0.20 |
| SM$_5$ | 0.025 | SM$_2$ | 0.27 |
| SM$_6$ | 0.050 | SM$_8$ | 0.30 |
| SM$_1$ }  SM$_4$ | 0.080 | SM$_9$ | 0.40 |
| SM$_5$ | 0.150 | SM$_{10}$ | 0.50 |
|  |  | SM$_{11}$ | 0.70 |
|  |  | SM$_{12}$ | 0.85 |
|  |  | SM$_{13}$ | 1.01 |

EXAMPLE 14

Test series M

With carrier SM$_4$, there is produced a catalyst formula M$_4$ containing rhodium, manganese and potassium.

Preparation of catalyst M$_4$: 100 g of SM$_4$ balls, moistened with 1% of H$_2$0, are impregnated with 0.6 g of rhodium (RhCl$_3$) and 3 ml of HCl (d=1.19) in 100 ml of water; after exhaustion of the solution, the catalyst is dried at 100° C. for 6 hours and then reduced with hydrogen for 3 hours at 280° C.

The catalyst is then impregnated with 6.91 g of potassium permanganate in saturated tepid aqueous solution; after drying at 150° C. for 3 hours and reduction at 400° C. for 2 hours, there is obtained a catalyst containing by weight:

Rh: 0.6%; MnO: 3%; K$_2$O: 2%

The results of the test conducted in the conditions of the series F mentioned at the end of example 8, are given in Table X series M.

EXAMPLE 15

Test series N

A catalyst N$_4$ containing rhodium, ruthenium and rhenium is prepared from a carrier SM$_4$: 100 g of SM$_4$ carrier are impregnated with 0.6 g of ruthenium and 0.3 g of rhodium in the form of chlorides, in the presence of 6 ml of HCl (d=1.19). After exhaustion of the impregnating solution, the washed carrier is dried at 100° C. for 2 hours, activated with air at 400° C. for 2 hours and then impregnated with 1% of rhenium in the form of ammonium perrhenate; after drying at 100° C. for 5 hours and reduction at 400° C. for 2 hours, there is obtained a catalyst containing by weight:

0.6% of ruthenium; 0.3% of rhodium; and 1% of rhenium.

The results of the test conducted in the conditions of series F are given in series N.

EXAMPLE 16

Test series O

A catalyst formula containing rhodium, ruthenium and iron is prepared in the following manner: 100 g of SM$_4$ carrier are contacted with 0.5 g of rhodium (RhCl$_3$) and 5 ml of HCl (d=1.19) in 100 ml of water. After exhaustion of the solution, the catalyst, dried at 100° C. for 4 hours and reduced at 300° C. for 2 hours, is impregnated in a dry state with 5% of Fe$_2$O$_3$ in the form of aqueous ferric chloride, dried at 200° C. for 2 hours and roasted at 450° C. for 2 hours. It is finally impregnated with 0.8% of Rb$_2$O in the form of aqueous carbonated rubidium hydroxide, then dried at 200° C. and roasted at 400° C. for 1 hour.

The results of the test in the conditions of series F, are reported in Table X series O.

EXAMPLE 17

Test series P

This example concerns a study of the performances of a catalyst formula P$_2$ containing rhodium, nickel and potassium on a carrier SM$_2$: 100 g of carrier SM$_2$ are impregnated with 3% of CoO (cobalt nitrate) then roasted for 10 hours at 600° C. The catalyst is then treated at 80° C. in a steam-oven saturated with water, then contacted with 0.6 g of rhodium (RhCl$_3$) in hydrochloric aqueous solution (5 ml HCl, d=1.19) up to exhaustion. After washing, drying at 200° C. for 2 hours and reduction at 400° C. for 1 hour, the catalyst is impregnated with 1.3% of K$_2$O in the form of di-potassium carbonate, then dried and activated under nitrogen atmosphere at 500° C. for 1 hour.

The results of the catalyst test performed in the conditions of the test of series F are reported in Table X series P. There is obtained substantially the same results by replacing the 3% of CoO with 3% of nickel oxide NiO.

EXAMPLE 18

Test series R

There is prepared as follows a catalyst formula containing ruthenium, palladium, nickel, iron and potassium on carriers SM$_1$ to SM$_{13}$: 100 g of carrier preimpregnated with 3% of NiO (nitrate), then calcined for 10 hours at 600° C., are impregnated with 0.4 g of palladium and 0.4 g or rhodium (introduced in the form of their chlorides) in 100 ml of a solution containing 6 ml of HCl. After exhaustion of the solution, the catalyst, dried at 150° C. for 3 hours and reduced at 350° C. for 2 hours, is impregnated with 3% of Fe$_2$O$_3$ (as a chloride), dried at 100° C. and then 200° C. for 2 hours and, finally, roasted at 500° C. for 4 hours; the final resulting catalyst mass is impregnated with 1.1% of K$_2$O (potassium carbonate) then dried at 200° C. for 1 hour and roasted at 350° C. for 2 hours.

There is thus obtained catalysts with reference numbers R, SM$_1$ to R, SM$_{13}$ which all contain, by weight:
0.4% of palladium
0.4% of rhodium
3% of Fe$_2$O$_3$
3% of NiO
1.1% of K$_2$O The catalysts R, SM$_1$ to R, SM$_{13}$ are tested in the conditions of the example of series F. The reaction temperature is increased so as to maintain the conversion rate at 65%. The temperature increase $\Delta T$ required for maintaining the conversion at 65% for 1000 hours, expressed in relation to the TiO$_2$ content of the carrier, is diagrammatically shown in the drawing. It is apparent that a $\Delta T \leq 26°$ C. may be obtained as soon as the TiO$_2$% (by weight) exceeds 0.05% (500 ppm) or better exceeds 0.06% (600 ppm) and preferably 0.07% (700 ppm), this $\Delta T$ increasing slightly for a TiO$_2$% greater than 0.3% (3000 ppm) and increasing beyond 5000 ppm (0.5%) of TiO$_2$.

TABLE II

Series No. B — Conversion = 45% by mole

| Carrier No. | TiO$_2$ % in the carrier | Metal 1 | Amount of Metal 1 | Metal or metal compound 2 | Amount of Metal 2 | Metal or metal compound 3 | Amount of Metal 3 | Catalyst number | Initial T | Final T | Deactivation over 1000 h | Benzene Yield Initial | Benzene Yield Final |
|---|---|---|---|---|---|---|---|---|---|---|---|---|---|
| SA$_1$ | 0.00 | Rh | 0.3% | Ru | 0.4% | K$_2$O | 1.8% | B$_1$ | 420 | 465 | 45 | 38.5 | 38 |
| SA$_3$ | 0.10 | Rh | 0.3% | Ru | 0.4% | K$_2$O | 1.8% | B$_3$ | 412 | 445 | 33 | 39.6 | 39.3 |
| SA$_5$ | 0.30 | Rh | 0.3% | Ru | 0.4% | K$_2$O | 1.8% | B$_5$ | 415 | 449 | 34 | 40.0 | 39.6 |
| SA$_7$ | 0.80 | Rh | 0.3% | Ru | 0.4% | K$_2$O | 1.8% | B$_7$ | 430 | 470 | 40 | 39 | 37.5 |

TABLE III

Series No. C — Conversion = 39.5% by mole

| Carrier No. | TiO$_2$ % in the carrier | Metal 1 | Amount of Metal 1 | Metal or metal compound 2 | Amount of Metal 2 | Metal or metal compound 3 | Amount of Metal 3 | Catalyst number | Initial T | Final T | Deactivation over 1000 h | Benzene Yield Initial | Benzene Yield Final |
|---|---|---|---|---|---|---|---|---|---|---|---|---|---|
| SA$_5$ | 0.30 | Rh | 0.3% | Pd | 0.4% | Na$_2$O | 1.8% | C$_5$ | 420 | 460 | 35 | 36.8 | 36.4 |

TABLE IV

Series No. D — Conversion = 44% by mole

| Carrier No. | TiO$_2$ % in the carrier | Metal 1 | Amount of Metal 1 | Metal or metal compound 2 | Amount of Metal 2 | Metal or metal compound 3 | Amount of Metal 3 | Catalyst number | Initial T | Final T | Deactivation over 1000 h | Benzene Yield Initial | Benzene Yield Final |
|---|---|---|---|---|---|---|---|---|---|---|---|---|---|
| SA$_4$ | 0.20 | Rh | 0.3% | Ir | 0.4% | Rb$_2$O | 0.8% | D$_4$ | 415 | 451 | 36 | 39.3 | 39.0 |

TABLE V

Series No. E — Conversion = 40% by mole

| Carrier No. | TiO$_2$ % in the carrier | Metal 1 | Amount of Metal 1 | Metal or metal compound 2 | Amount of Metal 2 | Metal or metal compound 3 | Amount of Metal 3 | Catalyst number | Initial T | Final T | Deactivation over 1000 h | Benzene Yield Initial | Benzene Yield Final |
|---|---|---|---|---|---|---|---|---|---|---|---|---|---|
| SA$_3$ | 0.10 | Rh | 0.3% | Pt | 0.4% | K$_2$O | 1.0% | E$_3$ | 421 | 461 | 40 | 36 | 35.1 |

TABLE VI

Series No. F — Conversion = 55% by mole

| Carrier No. | TiO$_2$ % in the carrier | Metal 1 | Amount of Metal 1 | Metal or metal compound 2 | Amount of Metal 2 | Metal or metal compound 3 | Amount of Metal 3 | Catalyst number | Initial T | Final T | Deactivation over 1000 h | Benzene Yield Initial | Benzene Yield Final |
|---|---|---|---|---|---|---|---|---|---|---|---|---|---|
| SF$_1$ | 0.00 | Rh | 0.5% | In | 0.3% | Na$_2$O | 1% | F$_1$ | 450 | 490 | 40 | 48.5 | 46.5 |
| SF$_2$ | 0.12 | Rh | 0.5% | In | 0.3% | Na$_2$O | 1% | F$_2$ | 450 | 485 | 35 | 49 | 48 |
| SF$_3$ | 0.12 | Rh | 0.5% | In | 0.3% | Na$_2$O | 1% | F$_3$ | 448 | 477 | 29 | 50.6 | 50.2 |

TABLE VII

Series No. G, H, I.

| Carrier No. | TiO$_2$ % in the carrier | Metal 1 | Amount of metal 1% | Metal or metal compound 2 | Amount of metal 2% | Metal or metal compound 3 | Amount of metal 3% | Toluene conversion % by mole | Catalyst number | Initial T. °C. | Final T. °C. | Deactivation over 1000 h °C. | Benzene Yield Initial | Benzene Yield Final |
|---|---|---|---|---|---|---|---|---|---|---|---|---|---|---|
| SF$_1$ | 0.00 | Rh | 0.35 | Ru | 0.35 | Ge | 1% | 50 | G$_1$ | 460 | 490 | 30 | 45.1 | 45 |
| SF$_3$ | 0.12 | Rh | 0.35 | Ru | 0.35 | Ge | 1% | 50 | G$_3$ | 462 | 477 | 15 | 46.1 | 47.2 |
| SF$_1$ | 0.00 | Rh | 0.6 | Sn | 0.4 | K$_2$O | 0.2% | 57 | H$_1$ | 470 | 505 | 35 | 53 | 51 |
| SF$_3$ | 0.12 | Rh | 0.6 | Sn | 0.4 | K$_2$O | 0.2% | 57 | H$_3$ | 467 | 490 | 23 | 53.3 | 52.6 |
| SF$_1$ | 0.00 | Rh | 0.30 | Pd | 0.40 | V$_2$O$_5$ | 5% | 68 | I$_1$ | 480 | 520 | 40 | 59.6 | 56.9 |
| SF$_3$ | 0.12 | Rh | 0.30 | Pd | 0.40 | V$_2$O$_5$ | 5% | 68 | I$_3$ | 470 | 490 | 20 | 60.2 | 60.1 |

TABLE VIII

Series No. J, K, L.    Toluene conversion = 60% by mole

| Carrier No. | TiO$_2$ % in the carrier | Metal 1 | Amount of metal 1% | Metal or metal compound 2 | Amount of metal 2% | Metal or metal compound 3 | Amount of metal 3% | Oxide 4 | Amount | Catalyst number | Initial T. | Final T. | Deactivation over 1000 h | Benzene Yield Initial | Final |
|---|---|---|---|---|---|---|---|---|---|---|---|---|---|---|---|
| SF$_3$ | 0.12 | Rh | 0.3 | Pd | 0.4 | Nb$_2$O$_5$ | 2 | Ta$_2$O$_5$ | 3 | J$_3$ | 462 | 480 | 18 | 53.9 | 53.4 |
| SF$_3$ | 0.12 | Rh | 0.55 | CrO$_3$ | 3 | K$_2$O | 1.5 | | | K$_3$ | 490 | 512 | 22 | 50.9 | 51.0 |
| SF$_3$ | 0.12 | Rh | 0.55 | MoO$_3$ | 3 | WO$_3$ | 1 | K$_2$O | 1.5 | L$_3$ | 485 | 507 | 22 | 51.0 | 50.0 |

TABLE X

Series No. M, N, O, P.

| Carrier No. | TiO$_2$ % in the Carrier | Metal 1 | Amount of metal 1% | Metal or metal compound 2 | Amount of metal 2% | Metal or metal compound 3 | Amount of metal 3% | Toluene conversion % by mole | Catalyst number | Initial T. °C. | Final T. °C. | Deactivation over 1000 h | Benzene Yield Initial | Final |
|---|---|---|---|---|---|---|---|---|---|---|---|---|---|---|
| SM$_4$ | 0.08 | Rh | 0.6 | MnO | 3 | K$_2$O | 2 | 50 | M$_4$ | 450 | 474 | 24 | 46.9 | 46.2 |
| SM$_4$ | 0.08 | Ru | 0.6 | Rh | 0.3 | Re | 1 | 60 | N$_4$ | 463 | 492 | 19 | 53.8 | 54.2 |
| SM$_4$ | 0.08 | Rh | 0.5 | Fe$_2$O$_3$ | 5 | Rb$_2$O | 0.8 | 70 | O$_4$ | 470 | 492 | 22 | 61.8 | 62.3 |
| SM$_2$ | 0.27 | Rh | 0.6 | CoO | 3 | K$_2$O | 1.3 | 73 | P$_2$ | 490 | 509 | 19 | 63.9 | 64.5 |

What we claim is:

1. A process for steam dealkylation of a charge containing at least one alkyl aromatic hydrocarbon, in the presence of a catalyst containing an alumina carrier and, expressed by weight with respect to the catalyst, from 0.1 to 1% of rhodium and 0.05 to 1% of titanium oxide TiO$_2$.

2. A process according to claim 1 wherein the catalyst contains, expressed by weight with respect to the catalyst, from 0.2 to 0.8% of rhodium and from 0.06 to 0.5% of titanium oxide.

3. A process according to claim 2, wherein the catalyst further contains, expressed by weight with respect to the catalyst, from 0.1 to 1% of at least one noble metal selected from ruthenium, palladium, iridium, platinum and osmium.

4. A process according to claim 2, wherein the catalyst further contains, expressed by weight, with respect to the catalyst, from 0.01 to 5% of at least one alkali metal selected from lithium, sodium, potassium, rubidium and cesium.

5. A process according to claim 3, wherein the catalyst further contains, expressed by weight with respect to the catalyst, from 0.01 to 5% of at least one alkali metal selected from lithium, sodium, potassium, rubidium and cesium.

6. A process according to claim 3, wherein the catalyst further contains, expressed by weight with respect to the catalyst, from 0.01 to 6% of at least one additional metal or compound of an additional metal selected from indium, zirconium, thorium, germanium, tin, vanadium, niobium, tantalum, chromium, molybdenum, tungsten, manganese, rhenium, iron, cobalt and nickel.

7. A process according to claim 6, wherein the catalyst contains a noble metal of the platinum family selected from ruthenium, palladium and platinum and in which the additional metal or metal compound is selected from rhenium, germanium, vanadium, tantalum and niobium.

8. A process according to claim 4, wherein the catalyst further contains, expressed by weight with respect to the catalyst, from 0.01 to 6% of at least one additional metal or compound of additional metal selected from indium, zirconium, thorium, germanium, tin, vanadium, niobium, tantalum, chromium, molybdenum tungsten, manganese, rhenium, iron, cobalt and nickel.

9. A process according to claim 8, wherein the catalyst contains an alumina carrier, from 0.25 to 0.65% of rhodium, 0.07 to 0.3% of titanium oxide, an alkali metal selected from sodium, potassium and rubidium, and at least one additional metal or compound of additional metal selected from indium, tungsten, tin, manganese, chromium, molybdenum, iron, niobium, cobalt, vanadium, nickel, germanium and iron.

10. A process according to claim 9, wherein the additional metal or the compound of additional metal of the catalyst is selected from cobalt, nickel, indium, tin, chromium, molybdenum, tungsten, manganese and iron.

11. A process according to claim 5, wherein the catalyst contains an alumina carrier and, by weight, from 0.25 to 0.65% of rhodium, 0.07 to 0.3% of titanium oxide, 0.25 to 0.65% of a noble metal selected from ruthenium, palladium and platinum, an alkali metal and 0.01 to 6% of at least one additional metal or compound of additional metal selected from indium, tungsten, tin, manganese, chromium, iron, niobium, cobalt, vanadium, nickel, germanium and rhenium.

12. A process according to claim 11, wherein the catalyst contains rhodium, titanium oxide, palladium, iron, nickel and potassium.

13. A process according to claim 1, used for the dealkylation of toluene to benzene.

14. A process according to claim 1, used for dealkylating alkylaromatic hydrocarbons issued from effluents of units for catalytic reforming or for producing aromatic hydrocarbons.

* * * * *